United States Patent [19]

Singh

[11] 4,058,511

[45] Nov. 15, 1977

[54] TEGRETOL ANTIGENS AND ANTIBODIES

[75] Inventor: Prithipal Singh, Sunnyvale, Calif.

[73] Assignee: Syva Company, Palo Alto, Calif.

[21] Appl. No.: 648,339

[22] Filed: Jan. 12, 1976

[51] Int. Cl.² ............................................. C07G 7/00
[52] U.S. Cl. ............................... 260/112 B; 23/230 B;
195/63; 195/66 R; 195/68; 195/103.5 A;
260/78 A; 260/112 R; 260/121; 424/12;
424/85; 424/88
[58] Field of Search ............... 260/112 R, 112 B, 121,
260/239 D; 195/63, 66, 68, 8 A

[56] References Cited

U.S. PATENT DOCUMENTS

| | | | |
|---|---|---|---|
| 2,948,718 | 8/1960 | Schindler | 260/239 D |
| 3,690,834 | 9/1972 | Goldstein et al. | 260/121 UX |
| 3,852,157 | 12/1974 | Rubenstein et al. | 195/63 |

*Primary Examiner*—Howard E. Schain
*Attorney, Agent, or Firm*—Townsend and Townsend

[57] ABSTRACT

Derivatives of dibenz[b,f]azepine drugs are provided for preparation of antigens and antibodies, the antibodies finding use in immunoassays for the dibenz[b,f]azepine drugs. Specifically, N-oxoaliphatic substituted carbamoyl dibenz[b,f]azepine compounds are provided which are conjugated with antigenic materials and injected into animals for production of antibodies specific for the azepine drug.

11 Claims, No Drawings

TEGRETOL ANTIGENS AND ANTIBODIES

BACKGROUND OF THE INVENTION

1. Field of the Invention

The subject invention is concerned with the preparation of derivatives of small haptenic compounds for use in conjugation to antigenic materials to provide antigens which when injected into vertebrates will produce antibodies which have high specificity for the particular haptenic compound. While there are a number of different ways in which a compound may be distinguished from other compounds of similar structure, one of the most versatile and accurate is the use of an antibody which is specific for a specific structure. That is, the binding constant of the antibody with a specific compound is substantially higher than its binding constant with other compounds of similar structure. By using this capability of antibodies, a wide number of different immunoassays have been developed. Among immunoassays which have found commercial acceptance are homogeneous enzyme immunoassays, spin labeled immunoassays, radioimmunoassays, and hemagglutination. Except for the last technique, each of the immunoassays depends upon the competition between the drug to be measured and a drug joined to a detector.

Since the compound of interest will only be modified to prepare the antigen, such modification must take into consideration the effect on the structural specificity of the antibody. That is, in choosing a site of conjugation between the drug and the antigen, it must be chosen so that the resulting product will provide antibodies which will recognize the original drug. Not only must the antibody recognize the original drug, but a significant characteristic of the drug must not be so changed that the antibody will recognize compounds closely related to the drug of interest. In addition, the conjugate of the drug to the antigen should provide high titers for the drug of interest and high binding constants for the drug of interest.

2. Description of the Prior Art

A review article on dibenzazepine compounds may be found in *Chemical Reviews*, 74, 101 (1974). U.S. Pat. No. 2,948,718 discloses derivatives of dibenzazepine which are reported to have pharmacological properties.

SUMMARY OF THE INVENTION

Dibenz[b,f]azepine compounds are conjugated to antigenic materials, particularly polypeptides and proteins, through an oxoaliphatic group, where the oxo group is bonded to the antigen and the alkyl group is bonded to the nitrogen of a carbamoyl group which in turn is bonded to the nitrogen of the azepine ring. Upon injection into vertebrates, these compounds are found to produce antibodies of high specificity for the drug Tegretol$^R$ (Carbamazepine). The compounds are prepared by reacting the dibenzazepine with phosgene, followed by reaction with an aminoalcohol. The alcohol is oxidized to an oxo group which may then be conjugated to an appropriate antigen, particularly a polypeptide or protein, through amine or alkylamine linkages.

DESCRIPTION OF SPECIFIC EMBODIMENTS

The compositions of this invention are N-derivatives of carbamazepine having an oxo functionality e.g. aldehyde or carboxy, bonded through an aliphatic chain of at least 1 carbon atom and not more than about 8 carbon atoms, more usually about 2 to 6 carbon atoms and from 0 to 1 heteroatom, which are chalcogen or nitrogen, particularly hetero of atomic number 7 to 8, wherein oxygen is present as oxy in the chain and nitrogen is present free of hydrogen atoms. The carboxy derivative is bonded primarily by peptide bonds to an antigen, such as a polypeptide or protein, and the aldehyde derivative by reductive amination is bonded through alkylamine bonds. The conjugated antigens are injected into a vertebrate, particularly a domestic animal, for production of antibodies. After a repeated number of injections based on a predetermined schedule, the antibodies may be harvested from the serum and may be used as obtained or further purified so as to concentrate the antibodies of interest.

For the most part, the compositions of this invention will have the following formula:

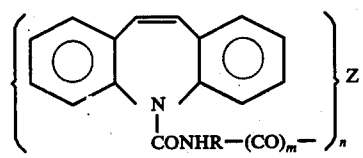

wherein:

$m$ is 0 or 1

R is a linking group, preferably an aliphatic linking group, of from 0 to 8 carbon atoms and 0 to 1 hetero atoms (chalcogen and nitrogen, preferably oxygen and nitrogen, and particularly preferred oxygen), the oxygen being present as oxy, and nitrogen being present free of hydrogen atoms, there being at least two carbon atoms between heteroatoms in the chain; which may be branched or straight chained, preferably straight chained, having from 0 to 1 site of ethylenic unsaturation as the only aliphatic unsaturation, with the proviso that R has at least 2 carbon atoms when $m$ is 0;

Z is hydrogen, hydroxyl, alkoxyl of from 1 to 6 carbon atoms, more usually of from 1 to 3 carbon atoms, alkyl carbonate ($OCO_2A$, wherein A is an alkyl group of from 1 to 6 carbon atoms, more usually from 1 to 4 carbon atoms), nitrophenoxy, particularly para or Y, wherein Y is a poly(amino acid), e.g. polypeptide residue (including polypeptide subunits of proteins); and $n$ is 1, except when Z is Y, when $n$ will be equal to the number of acyl groups bonded to the amino and tyrosine groups of Z, $n$ being at least 1, and not greater then the number of amino and tyrosine functional groups available for bonding, usually not more than the molecular weight of Y divided by 500, more usually not more than the molecular weight of Y divided by 1500, and usually at least one per 100,000 molecular weight.

Preferred R groups include alkylene, alkenylene, alkyleneoxyalkylene (wherein the alkylene groups are separated by at least two carbon atoms), N-lower alkyl (1-3 carbon atoms), alkyleneaminoalkylene (wherein the alkylene groups are separated by at least two carbon atoms).

The compounds of primary interest are those where Z is Y and find use as antigens, Y being an antigenic poly(amino acid). These compounds will for the most part have the following formula:

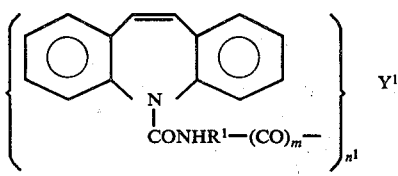

wherein:

m is 0 or 1

R[1] is a bond or an aliphatic radical of from 1 to 8 carbon atoms, more usually of from 2 to 6 carbon atoms, normally of at least 2 carbon atoms when m is 0, having from 0 to 1 site of ethylenic unsaturation as the only unsaturation and from 0 to 1 heteroatom which is oxygen and nitrogen, usually bonded solely to carbon, particularly oxygen as oxy in the chain, and may be branched chain or straight chain, preferably straight chain, i.e. polymethylene;

Y[1] is an antigenic poly(amino acid) of at least 1,000 molecular weight, more usually of at least 10,000 molecular weight and may be of molecular weight of 10 million or greater, generally not exceeding about 500,000 molecular weight; and n[1] is at least 1, usually greater than 1, and generally not exceeding the molecular weight of Y[1] divided by 500, more usually by 1,000 and preferably by about 2,000 and will be at least the molcular weight of Y[1] divided by 100,000, more usually the molecular weight of Y[1] divided by 50,000.

With intermediate molecular weight antigens, those having molecular weights in the range of 20,000 to 1 million, the number will generally be up to about 250, more usually 4 to 100. With low molecular weight antigens (1,000 to 5,000 molecular weight) the number will be about 1 to 10, usually 2 to 5.

As indicated previously, of particular interest are compounds where the oxo-carbonyl group (other than keto) and the non-oxo-carbonyl group are bonded to an amino group, which is part of a polypeptide or protein structure. One group of polypeptides and proteins is antigenic, so that by bonding the carbonyl derivative of dibenzazepine to the polypeptide or protein, antibodies can be formed to dibenzazepine. A narrower class of proteins, which also can be used as antigens, but will not normally be used as such, are enzymes which are employed as the detector in an immunoassay system. As antigens, inactive enzymes can be used.

Polypeptides (referred to generally in the invention as poly(amino acid)) usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 amino acid groups (or 10,000 to 35,000 molecular weight). For the purposes of this invention, poly(amino acid) is intended to include individual polypeptide units and polypeptides which are subunits of proteins, whether composed solely of polypeptide units or polypeptide units in combination with other functional groups, such as porphyrins, as in haemoglobin or cytochrome oxidase.

The number of dibenzazepine groups will vary depending upon whether the poly(amino acid) is an enzyme or antigen. The maximum number of groups will be limited by the effect of substitution on solubility, activity, and the like. For the formation of antibodies, a sufficient number of dibenzazepine groups should be present, so as to provide a satisfactory harvest of antibodies to the dibenzazepine. Otherwise, the proportion of antibodies to dibenzazepine as compared to antibodies to other compounds may be undesirably low.

The first group of protein materials or polypeptides which will be considered are the antigenic polypeptides. These may be joined to the carbonyl group of the dibenzazepine analog through an amino group. The product can be used for the formation of antibodies to dibenzazepine. The protein materials which may be used will vary widely, and will normally be from 1,000 to 10 million molecular weight, more usually 20,000 to 500,000 molecular weight.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended when speaking of enzyme molecular weights to refer to the entire enzyme. There will be on the average at least about one dibenzazepine per enzyme, usually at least about two dibenzazepines per enzyme, when the labeling is not limited to a specific amino group, and rarely more than 40 dibenzazepines per enzyme, usually not more than 30 dibenzazepines per enzyme. For example, with lysozyme the average number of dibenzazepine groups will be in the range of about 2 to 5. For glucose-6-phosphate dehydrogenase the average number will be in the range of 2 to 20.

While the dibenzazepine analog may be bonded through the non-oxo-carbonyl group to hydroxyl or mercapto groups, which are present in the proteins, for the most part the bonding will be to amino. Therefore, the compounds are described as amides, although esters and thioesters may also be present. The aldehyde derivative will be bonded solely to amino to form alkylamine groups through reductive amination.

Amino acids present in proteins which have free amino groups for bonding to the carboxy modified dibenzazepine includes lysine, N-terminal amino acids, etc. The hydroxyl and mercaptan containing amino acids include serine, cysteine, tyrosine and threonine.

Various protein and polypeptide types may be employed as the antigenic material. These types include albumins, enzymes, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tyrosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the carbonyl modified dibenzazepine may be conjugated. As indicated, the dibenzazepine modified enzyme is useful for immunoassays. A description of the immunoassay technique will follow.

Various enzymes may be used such as peptidases, esterases, amidases, phosphorylases, carbohydrases, oxidases, e.g. dehydrogenase, reductases, and the like. Of particular interest are such enzymes as lysozyme, peroxidase, α-amylase, dehydrogenases, particularly malate dehydrogenase and glucose-6-phosphate dehydrogenase, alkaline phosphatase, α-glucuronidase, cellulase and phospholipase. In accordance with the I.U.B. Classification, the enzymes of interest are: 1. Oxidoreductases, particularly Groups 1.1, and more particularly 1.1.1, and 1.11, more particularly, 1.11.1; and 3. Hydrolases, particularly 3.2, and more particularly 3.2.1.

The substituted enzymes will for the most part have the following formula:

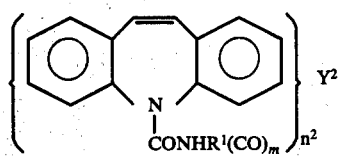

wherein:
  $m$ and $R^1$ have been defined previously;
  $Y^2$ is an enzyme substituted at other than the active site, and having at least 30, preferably at least 50 percent of its original activity prior to conjugation; and
  $n^2$ will usually be of from 1 to 50, more usually from 2 to 35, preferably 2 to 14, more preferably 2 to 12, but generally on the average not more than about 60 percent of the total lysine groups available in the enzyme, although small enzymes such as lysozyme may have all available lysine groups conjugated.

Instead of an enzyme a stable free radical may be employed as the functionality for detection in the immunoassay. The stable free radicals are cyclic nitroxides having the nitrogen of the nitroxide as an annular member, from 0 to 1 other heteroatoms, i.e. oxygen and nitrogen, as annular members. The stable free radical molecules bonded to the non-oxo-carbonyl of the dibenzazepine derivatives will normally be from 7 to 16 carbon atoms, more usually from 7 to 12 carbon atoms. The amino functionality may be bonded directly to the annular carbon atom or may be bonded to the ring through an aliphatic chain of from 1 to 4 carbon atoms, more usually of from 1 to 2 carbon atoms. The molecules may have from 0 to 2 sites of ethylenic unsaturation, more usually from 0 to 1 site of ethylenic unsaturation as the only unsaturation.

For the most part, the stable nitroxide functionalities bonded to the nonoxocarbonyl of the derivatized dibenzazepine will have the following formula:

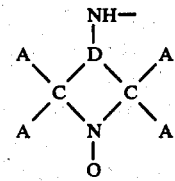

wherein:
  D is a divalent aliphatic radical usually aliphatically saturated of from 1 to 6 carbon atoms, more usually of from 1 to 3 carbon atoms, only from 1 to 3, usually 2 to 3 of the carbon atoms in D being annular atoms; and
  A is lower alkyl (1 to 6, usually 1 to 3 carbon atoms), particularly methyl.

For the most part, compounds are pyrrolidine or piperidine derivatives, and D is hydrocarbon.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile and hexamethylphosphoramide. The reaction is carried out by bringing the various reagents together under mild conditions and allowing sufficient time for the reaction to occur.

A second method is to form a mixed anhydride employing an alkyl chloroformate, e.g. isobutyl chloroformate. The mixed anhydride is formed by combining the carboxy substituted dibenzazepine, the alkyl chloroformate and tertiary amine. The temperature is normally below ambient temperature.

At least a stoichiometric amount of the chloroformate is employed based on the dibenzazephine derivative, and usually an excess, which usually does not exceed three times stoichiometric. The tertiary amine is present in at least equimolar amount to the chloroformate.

The mixture is then combined with the amino compound to be conjugated and the reaction allowed to proceed under mild conditions.

Also, esters of the carboxy modified dibenzazepine can be employed which are operative in water for acylating amine functions. An illustrative hydroxylic group is p-nitrophenyl which can be used to prepare the p-nitrophenyl ester. For the aldehyde conjugation, a reductive amination is carried out in a polar, usually aqueous medium, employing sodium cyanoborohydride as the reducing agent.

The antibodies which are prepared in response to the conjugated antigens of this invention have strong specific binding to the parent drug, the conjugated antigen, the compound or derivative thereof used to conjugate to the antigen, the acid labeled compounds, e.g. enzyme conjugate and spin label conjugate.

EXPERIMENTAL (The following examples are offered by way of illustration and not by way of limitation. All temperatures not indicated are in Centigrade.)

EXAMPLE I

N-chlorocarbonyl dibenz[b,f]azepine

To a slurry of 14.10g (0.073 mole) of dibenz[b,f]azepine in 60ml of dry toluene at room temperature was added dropwise a 120ml solution of 12.5% phosgene (excess) in benzene over 45 minutes. The resulting yellow slurry was stirred for 2 hours at room temperature, heated to reflux an additional 2 hours, and then stirred at room temperature overnight. Concentration of the reaction mixture by rotary evaporator in the hood gave a pale yellow solid which was taken up in 200ml benzene and treated with Norit-A$^R$ at boiling. The hot solution was filtered through celite, concentrated to one half of its original volume, cooled to room temperature and petroleum ether added to turbidity; white crystals of the named product precipitated. Yield, 14.4g, m.p. 145°–150°. Recrystallization from benzene-hexane afforded needles m.p. 150°–156.5°.

EXAMPLE II 5-(N-[6'-hydroxyhexyl]carbamoyl)-dibenz[b,f]azepine

To 3.85g (0.015mole) of the acid chloride (Ex. I) in 100ml of dry benzene was added 7.2g (0.62mole) of 6-aminohexanol suspended in 200ml of dry benzene. The reaction mixture was refluxed for 24 hours while protected from atmospheric moisture with a drying tube. The resulting solution was cooled, washed with aqueous 10% HCl, saturated aq. $Na_2CO_3$, then with water and dried ($MgSO_4$). Evaporation of the solvent gave 5g of crude alcohol product.

EXAMPLE III 5-(N-[3'-hydroxypropyl]carbamoyl)-dibenz[b,f]azepine

To a slurry of 3.83g (0.015mole) of acid chloride (Ex. I) in 200ml of dry benzene was added 4.5g (0.6mole) of 3-aminopropanol. This mixture was allowed to sit overnight and then refluxed for 24 hours. The resulting yellow solution was cooled, washed with 50ml of aqueous 2.5% HCl, 50ml of saturated aqueous $Na_2CO_3$ and then with water. The benzene solution was dried ($MgSO_4$), concentrated to give one half of its original volume, petroleum ether added to turbidity and the mixture cooled to give 2.75g (63%) of product: m.p. 129°–130°.

EXAMPLE IV 5-(N-[5'-carboxypentyl]carbamoyl)-dibenz[b,f]azepine

A. To a solution of 1.90g (5.6mmol) of alcohol (Ex. II) in 25ml of acetone, cooled in an ice bath, was added 7.0ml of Jones reagent (ca. 1.5g of $CrO_3$ in $H_2SO_4$) slowly, maintaining the reaction mixture between 0° to 5°. After stirring at this temperature for 1.5 hours, excess Jones reagent was destroyed by adding 20ml of isopropyl alcohol and stirring for an additional 30 minutes. The resulting reaction mixture was filtered and the filtrate was concentrated and purified by preparative TLC (10% MeOH/90% $CHCl_3$) to give 1.40g (65%) of crude acid product. Further purification by crystallization from methanol-water with difficulty and drying at 0.1mm over $P_2O_5$ at 39° for 3 days gave material: m.p. 135°–136°.

B. To the slurry of 144mg (1.1mmol) of ε-aminocaproic acid in 70ml dry benzene and 3ml of dry triethylamine at room temperature was added 256mg (1mM) of the product of Ex. I in one portion. The reaction mixture was refluxed overnight, cooled and concentrated to dryness. The resulting residue was taken up in 70ml of $CHCl_3$, washed with 2×10ml of water, once with saturated brine and dried ($MgSO_4$). Concentration of the filtered chloroform solution gave an orange yellow oil which weighed 347mg. Crystallization (ethyl acetate-cyclohexane) gave 61mg of pure product.

EXAMPLE V

Preparation of 5-(N-2'-carboxyethyl carbamoyl)-dibenz[b,f]azepine

To a solution of 2.0g (6.8mmol) of the N-propyl alcohol (Ex. III) in 25ml of acetone cooled to 0°, was added dropwise 9ml of Jones reagent ($CrO_3$, 2.7g; $H_2SO_4$, 2.5ml; $H_2O$, 7ml) and stirred at 0° to 5° for 90 minutes. Excess Jones reagent was destroyed by addition of 20ml of isopropyl alcohol. The green mixture was filtered, extracted first with 200ml of $CHCl_3$, and then again with 250ml of $CHCl_3$. The combined $CHCl_3$ extracts were extracted with 50ml of saturated $NaHCO_3$. The bicarbonate extract was washed with 25ml of $CH_2Cl_2$ and then acidified with concentrated HCl at 0° to give the product as a pale solid. The solid was washed once with a few ml of ice cold $H_2O$, filtered and dried (desiccator), 1.33g, 64% yield. Recrystallization from ethyl acetate-hexane gave the product as colorless crystals: m.p. 164°–165°.

EXAMPLE VI

Preparation of 5-(N-[5'-(N'-[2",2",5",5"-tetramethyl-1"-oxylpyrrolidinyl-3"]formamido)-dibenz[b,f]azepine To a solution of 112mg (0.32mmol of the carboxypentyl acid (Ex. IV) in 2ml of dry DMF, cooled to −12° by a dry ice-acetone bath, was added 100μl (ca. 1mmol) of $Et_3N$. The reaction mixture was stirred for 30 minutes and 70μl (0.5mmol) of isobutyl chloroformate added. A solution of 66mg (0.4mmol) of spin label amine (2,2,5,5-tetramethyl-3-amino-1-oxy-pyrrolidine) in 2ml of dry DMF was added, the resulting reaction mixture was stirred at −10° for an hour and at room temperature overnight. The DMF and excess solvents were stripped off at 0.5mm in a warm water bath. The yellow residue was taken up in 50ml of $CH_2Cl_2$, washed with 3×10ml of $H_2O$, then saturated brine, dried ($MgSO_4$) and concentrated give the product as a yellow semi-solid (260mg). The crude product was treated with ethyl acetate and hexane at room temperature to give a pale yellow solid (91mg, 59%). Recrystallization from ethyl acetate-hexane yielded analytically pure material: m.p. 169°–170°.

EXAMPLE VII

Conjugation of 5-(N-[5'-carboxypentyl-1']carbamoyl)-dibenz[b,f]azepine to bovine serum albumin (BSA)

To a solution of 140mg (0.4mmol) of the carboxypentyl acid (Ex. IV) in 7ml of dry DMF (in a 25ml R.B. flask fitted with a serum cap) at −10° to −15° was added 70μl of $Et_3N$ (ca. 0.5mmol) followed by addition of 62μl (ca. 0.5mmol) of isobutyl chloroformate. The resulting white slurry was stirred for 2 hours at −10° to −15°.

The above mixed anhydride was added over a period of 30 minutes to a solution of 220mg (ca. 0.003mmol) of BSA in 15ml of water and 0.05 N NaOH at pH 8.5–9.0 in an ice bath (pH of the reaction mixture was maintained at 8.5 with dilute aqueous NaOH) and stirred in the cold room for an additional 2 hours. The resulting reaction mixture was slightly turbid. This solution was dialyzed against 4 l. of 0.1M $NaHCO_3$–0.1M $Na_2CO_3$ buffer three times at 12 hour intervals and the process was repeated with water.

The dialyzed solution was filtered through a 0.22μ millipore filter, centrifuged for an hour at 10,000 RPM and lyophilized in a sterilized lyophilization flask to give 155mg of the conjugate. UV analysis of the conjugate showed the presence of 39 haptens in this conjugate.

EXAMPLE VIII

Conjugation of 5-(N-[2'-carboxyethyl-1']-carbamoyl)-dibenz[b,f]azepine to bovine serum albumin (BSA)

To a stirring solution of 305mg (0.001m) of N-(2-carboxyethylcarbamoyl)5-H-dibenz[b,f]azepine in dry DMF (4A molecular sieves) at −5° C was added 139μl (0.001m) triethylamine followed by 126μl (0.001m) isobutyl chloroformate. This mixture was stirred for 1.5 hours at −5° after which time it was added dropwise over a period of 5 minutes to a cooled solution (0°) of 1.0gm BSA in 20ml DMF and 50ml 0.1M carbonate, pH9. This reaction was stirred overnight in the cold room. Dialysis (2X) against 4l. of 0.05M carbonate, pH 9 and then twice against 4l. of pH 9.5 aqueous ammonia, followed by lyophilization afforded 1.035gm of the desired product with a hapten number of 30 as calculated by UV.

EXAMPLE IX

Conjugation of 5-(N-[5'-carboxypentyl-1']carbamoyl)-dibenz[b,f]azepine to glucose-6-phosphate dehydrogenase (G-6-PDH)

A. Into a reaction flask was introduced 8.4mg (0.05mmol) of the carboxypentyl derivative of Ex. IV in 125μl of DMF, and equimolar amounts of carbitol chloroformate and triethylamine added, while the temperature was maintained at about −20° C.

The above mixture is then added slowly to a solution of 1.9mg/ml of glucose-6-phosphate dehydrogenase in 0.055M tris buffer at pH 8.1 containing 0.3ml DMF in the presence of 10mg of glucose-6-phosphate and 20mg NADH at a temperature of 4°. The pH was maintained between 8 and 9 by the addition of 1N sodium hydroxide requiring about 200ml. The product was then dialyzed against 0.055M tris, pH 8.1 for 40 hours (4×2 l.), leaving 3ml of dialysate.

B. The assay procedure for determining percent deactivation and percent inhibition is as follows: Two parts by volume of a solution 0.1M NAD, pH 5-6 is combined with three parts by volume of 0.11M glucose-6-phosphate in 0.055M tris-HCl buffer, pH 7.9. An aliquot of the dialyzed conjugate is diluted 1:100 with the above-indicated buffer. An assay solution is formed from 50μl of the (G-6-P)-NAD solution, 750μl of buffer, 50μl of buffer or buffer containing antibody, depending upon whether deactivation or inhibition was being determined, and 50μl of the enzyme conjugate or enzyme control. Portions of buffer are employed to ensure quantitative transfers. The solution is aspirated into a spectrometer and the rate of NADH production followed at 340nm at 30° C. The change in OD per minute is determined between the second and third minutes. The enzyme conjugate was found to be 88% deactivated and 65% inhibited.

C. An assay was carried out with varying amounts of Tegretol. The assay is carried out as follows: a 50μl sample is dispensed with 250μl buffer (pH 8.1 at 25° C; 0.55M tris-HCl; 0.05% w/v sodium azide; 0.005% w/b Thimerosal) containing 0.5% sodium chloride; and 0.01% v/v Triton X-100 (saline buffer) into a 1 ml cup. After 60 seconds of equilibration, 50μl of the above sample solution is dispensed in a second cup to which is added 50μl of antibody solution in buffer containing 1% w/v rabbit serum albumin, 0.066M glucose-6-phosphate and 0.4M NAD monosodium salt, followed by 250μl of saline buffer. Finally, 50μl of the enzyme conjugate in buffer containing 0.9% w/v NaCl and 1% w/v rabbit serum albumin is added followed by the addition of 250μl of buffer. The assay mixture is aspirated into a spectrometer cell and after a 15 second delay a first absorbance reading is made, and 80 seconds later a second absorbance reading is made. The difference between the readings is reported as OD units. Using samples of known Tegretol concentration, the difference between no Tegretol and 1μg/ml concentration was 11 OD units and the difference between no Tegretol and 10μg/ml was 51 units.

EXAMPLE X

Preparation of 5-carbamyl(N-propanalyl)-5H-dibenz[b,f]azepine

To a rapidly stirring solution of 9.7ml (0.012m) dry (4A molecular sieves) pyridine in 150ml dry CH$_2$Cl$_2$(3A molecular sieve) was added 6.0g (.06mol) dried CrO$_3$. This solution was stirred in an ice bath for 30 minutes protected from moisture by a drying tube. N-(3-hydroxypropylcarbamoyl)5-H-dibenz[b,f] azepine (2.91g. .01m) in 7ml CH$_2$Cl$_2$ was added in one shot and the reaction mixture stirred at room temperature for 45 minutes. The solution was poured out of the flask and the tarry residue rinsed with 150ml CH$_2$Cl$_2$. The solutions were combined and washed successively with 3×10ml 1N NaOH, 3×100ml 1N HCl, 3×100ml saturated NaHCO$_3$, saturated brine and then dried over Na$_2$SO$_4$. All wash solutions were back washed with either. The ether back washings and the CH$_2$Cl$_2$ solutions were combined and the product was stripped off the solvent. The oily residue crystallized on standing to afford 1.71g of the title compound (59%). Recrystallization from benzene-petroleum ether furnished white crystals, m.p. 121°-122.5°.

EXAMPLE XI

Conjugation of 5-carbamyl-N-propanyl)-5H-dibenz[b,f]azepine to BSA

To a cooled (5°) solution of 600mg BSA (Pentex recrystallized) in 40ml of (1.02M) pH 7 phosphate buffer was added 294mg (0.001m) of the aldehyde of Ex. X in 5ml methanol. Following the addition, 2ml more methanol was added to effect solution. To the slightly cloudy mixture was added 68mg (0.0011m) sodium cyanoborohydride and the pH adjusted to 7.3 by addition of KH$_2$PO$_4$. This reaction mixture was stirred in the cold room for 40 hours, then at room temperature for 4 hours before being spun down. The precipitate was resuspended in 8M urea and this solution, after centrifugation, was combined with the supernatant and dialyzed 0.05M Na$_2$CO$_3$, pH 9 and 2×4l. pH 9.5 NH$_4$OH. Lyophilization afforded 588mg of conjugate with a hapten number of 28 as determined by UV.

EXAMPLE XII

Conjugation of 5-carbamyl(N-propanalyl)-5H-dibenz[b,f]azepine to BGG

Methanol (15ml) was added to an 80ml solution of 600mg bovine gamma globulin (Pentex fraction II) in 0.2M phosphate, pH7. This solution was cooled to 5° before 293mg (0.001m) of the aldehyde (Ex. X) in 5ml methanol was added followed closely by 68mg (0.0011m) sodium cyanoborohydride. This mixture was stirred in the cold room for 1 day, then at room temperature for a second day. The mixture was spun down and the supernatant combined with the resuspended precipitate in 9M urea. The conjugate was dialyzed against: 1×2l. 6M urea — 0.05M carbonate pH 9; 1×2l. 4M urea — 0.05 carbonate pH 9; 1×2M urea — 0.05M carbonate pH 9; 2×4l. 0.05M carbonate pH 9; and finally 2×4l., pH 10 NH$_4$OH. The solution was spun down after dialysis and lyophilized to give 226mg of conjugate with a hapten number of 18 as determined by U.V.

In order to demonstrate the effectiveness of the subject compositions in an assay, antibodies were prepared employing the antigen of Example VIII. In carrying out the assay, buffer is employed which is 0.055M tris-HCl, pH 8.1 at 25° C; 0.05% w/v sodium azide; 0.005% w/v Thimerosal; and 2.0 weight percent sodium chloride (w/v is grams per 100ml). The assay is carried out by transfering 50μl of the sample e.g. serum, to a cup with 250μl of buffer, followed by the addition of 50μl of antibody solution in buffer containing 1% w/v rabbit serum albumin, 0.066M glucose-6-phosphate and 0.4M NAD (monosodium salt), followed by 250μl of buffer. Finally, 50μl of the enzyme conjugate of Example IX in buffer containing 0.9% w/v NaCl and 1% w/v rabbit serum albumin is added followed by the addition of 250μl of buffer. The assay mixture is aspirated into a spectrometer cell and after a 15 second delay a first absorbance reading is made and 80 seconds later a second absorbance reading made. The temperature of the cell is 30° C. The difference between the readings is reported as OD units times $10^3$. A separation of 20 OD units is obtained between a sample having no Tegretol and 1μg per milliliter Tegretol.

In a cross-reactivity study, iminostilbene required greater than about 167μg/ml for a response equivalent to 1ng/ml of Tegretol, while other compounds of similar structure such as carbamazepine-10,11 epoxide, imipramine, amitriptyline and desmethyl imipramine did not show an equivalent response to 1ng/ml of Tegretol at greater than 1000μg/ml.

The above data show that in accordance with this invention, antibodies can be prepared which are highly sensitive to Tegretol and specific to the Tegretol structure. In addition, a sensitive assay can be developed employing the Tegretol derivatives conjugated to an enzyme, such as glucose-6-phosphate dehydrogenase.

Although the foregoing invention has been described in some detail by way of illustration and example for purposes of clarity of understanding, it will be obvious that certain changes and modification may be practiced within the scope of the appended claims.

What is claimed is:

1. A compound of the formula:

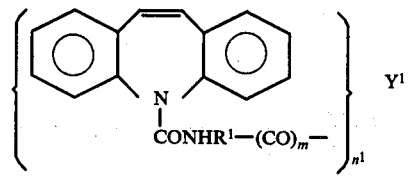

wherein:

$m$ is 0 or 1, $R^1$ is a bond or an aliphatic radical of from 1 to 8 carbon atoms having from 0 to 1 site of ethylenic unsaturation as the only unsaturation and from 0 to 1 heteroatom of atomic number 7 to 8 bonded solely to carbon with the proviso that $R^1$ has at least 2 carbon atoms when $m$ is 0;

$Y^1$ is an antigenic poly(amino acid) of at least 1,000 molecular weight; and $n^1$ is at least 1 and not greater than the molecular weight of $Y^1$ divided by 500, with the proviso that when $m$ is 0 $R^1$ is bonded to amino groups of said poly(amino acid) by a single covalent bond to form an alkylamino and when $m$ is 1 the carboxy carbonyl is bonded to amino groups of said poly(amino acid) by a single covalent bond to form an amide.

2. A compound according to claim 1, wherein $Y^1$ is of molecular weight in the range of about 10,000 to 500,000 and $n^1$ is in the range of about 4 to 250.

3. A compound according to claim 2, wherein $Y^1$ is an albumin.

4. A compound according to claim 2, wherein $Y_1$ is a globulin.

5. A compound according to claim 2, wherein $R^1$ is polymethylene of from 2 to 6 carbon atoms.

6. A compound according to claim 2 wherein $Y^1$ is an albumin or globulin, $R^1$ is polymethylene of 3 carbon atoms and $m$ is 0.

7. A compound according to claim 2 wherein $Y^1$ is albumin or globulin, $R^1$ is polymethylene of 2 carbom atoms and $m$ is 1.

8. A compound according to claim 2, wherein $Y^1$ is albumin or globulin, $R^1$ is polymethylene of 5 carbon atoms and $m$ is 1.

9. Antibodies prepared in response to a compound according to claim 1.

10. Antibodies prepared in response to a compound according to claim 2.

11. Antibodies prepared in response to a compound according to claim 5.

* * * * *

UNITED STATES PATENT OFFICE
CERTIFICATE OF CORRECTION

Patent No. 4,058,511            Dated November 15, 1977

Inventor(s) Prithipal Singh

It is certified that error appears in the above-identified patent and that said Letters Patent are hereby corrected as shown below:

IN THE TITLE:

change "Tegretol" to --Carbamazepine--

Signed and Sealed this

Twenty-seventh Day of June 1978

[SEAL]

Attest:

RUTH C. MASON
*Attesting Officer*

DONALD W. BANNER
*Commissioner of Patents and Trademarks*